(12) United States Patent
Jokerst et al.

(10) Patent No.: US 12,588,888 B2
(45) Date of Patent: Mar. 31, 2026

(54) HIGH-RESOLUTION ULTRASONOGRAPHY OF GINGIVAL BIOMARKERS FOR PERIODONTAL DIAGNOSIS IN HEALTHY AND DISEASED SUBJECTS

(71) Applicant: THE REGENTS OF THE UNIVERSITY OF CALIFORNIA, Oakland, CA (US)

(72) Inventors: Jesse Vincent Jokerst, La Jolla, CA (US); Colman Arthur Moore, La Jolla, CA (US); Casey Chen, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 9 days.

(21) Appl. No.: 18/706,898

(22) PCT Filed: Nov. 7, 2022

(86) PCT No.: PCT/US2022/049082

§ 371 (c)(1),
(2) Date: May 2, 2024

(87) PCT Pub. No.: WO2023/081438

PCT Pub. Date: May 11, 2023

(65) Prior Publication Data

US 2025/0032087 A1     Jan. 30, 2025

Related U.S. Application Data

(60) Provisional application No. 63/276,135, filed on Nov. 5, 2021.

(51) Int. Cl.
*A61B 8/08*        (2006.01)
*A61C 19/04*      (2006.01)

(52) U.S. Cl.
CPC .......... *A61B 8/0858* (2013.01); *A61B 8/0833* (2013.01); *A61B 8/0875* (2013.01); *A61C 19/04* (2013.01)

(58) Field of Classification Search
CPC ... A61B 8/0858; A61B 8/0833; A61B 8/0875; A61C 19/04
See application file for complete search history.

(56)      References Cited

U.S. PATENT DOCUMENTS 5,755,571 A  *  5/1998  Companion  ......... A61C 19/043
                                                                      33/514
7,156,655 B2 *  1/2007  Sachdeva  ............. A61C 9/0046
                                                                      433/213

(Continued)

FOREIGN PATENT DOCUMENTS

CN         110680402 A       1/2020

OTHER PUBLICATIONS

Chifor et al; "Periodontal evaluation using a non-invasive imaging method (ultrasonography)"; Medicine and Pharmacy Reports 2019 vol. 92—Supplement No. 3 / S20-S32 (Year: 2019).*

(Continued)

*Primary Examiner* — Dixomara Vargas
(74) *Attorney, Agent, or Firm* — Kaplan Breyer Schwarz LLP

(57)         ABSTRACT

A method for measuring periodontal disease and treating diseases associated therewith includes: obtaining B-mode ultrasound images of a dentition and periodontium of a patient; identifying gingival margin (GM), alveolar bone crest (ABC), cementoenamel junction (CEJ), periodontal ligament (PDL), and gingival edge (GE) biomarkers on the B-mode ultrasound images, the GE biomarker being a part of periodontal soft tissue most distal from a tooth surface; evaluating a metric associated with periodontal disease using one or more of the GM, ABC, CEJ, PDL and GE (Continued)

1. CLINICAL DENTAL EXAM
2. ULTRASOUND IMAGING biomarkers and based at least in part on the evaluating, performing an act that implements and/or adjusts a therapeutic treatment of a periodontal disease.

8 Claims, 11 Drawing Sheets

(56) References Cited

U.S. PATENT DOCUMENTS

| | | | | |
|---|---|---|---|---|
| 2017/0037450 A1* | 2/2017 | Zourob | ........... | G01N 33/54326 |
| 2021/0093200 A1* | 4/2021 | Jokerst | ................ | A61B 5/0062 |
| 2021/0343400 A1* | 11/2021 | Inam | ...................... | G16H 10/60 |
| 2023/0030704 A1* | 2/2023 | Weinstein | .............. | A61B 5/682 |
| 2023/0320817 A1* | 10/2023 | Leviton | ................. | G16H 80/00 |
| | | | | 433/24 |
| 2023/0365662 A1* | 11/2023 | Nara | .................. | C07K 16/1203 |
| 2024/0400654 A1* | 12/2024 | Nara | ....................... | A61P 31/04 |
| 2025/0104868 A1* | 3/2025 | Kolli | ...................... | A61B 6/463 |

OTHER PUBLICATIONS

Tim Jewell; "Gum Tissue Graft: Why It's Needed and What to Expect"; (Year: 2017).*
Figueredo et al.; "Ultrasound Imaging of the Periodontium Complex: A Reliability Study"; International Journal of Dentistry vol. 2023, Article ID 5494429, 10 pages (Year: 2023).*
Le et al.; "Ultrasound for Periodontal Imaging"; Book; Chapter 5 (Year: 2020).*
Chifor, "Periodontal evaluation using a non-invasive imaging method (ultrasonography)" Dental Medicine, Sep. 30, 2019.

* cited by examiner

1. CLINICAL DENTAL EXAM
2. ULTRASOUND IMAGING

US GEL

DISPOSABLE COVER

IMAGING ACCESSIBLE

HIGH-RESOLUTION ULTRASONOGRAPHY OF GINGIVAL BIOMARKERS FOR PERIODONTAL DIAGNOSIS IN HEALTHY AND DISEASED SUBJECTS

GOVERNMENT FUNDING

This invention was made with government support under DE029025, DE029917, and TR001442, awarded by the National Institutes of Health. The government has certain rights in the invention.

BACKGROUND

Nearly 50% of Americans have periodontitis resulting in pain, tooth loss, reduced quality of life and even systemic effects like cardiovascular disease, but tools to diagnose/monitor periodontitis have major limitations. Clinical assessment (by periodontal examination) and radiography are currently the standard of care but are time-consuming for the clinician, uncomfortable for the patient, and subject to large errors—interexaminer variation in probing can be >40%. Moreover, clinical assessment and radiographic examination may not capture all clinical information (e.g., gingival thickness and inflammation).

The periodontal examination provides critical information such as probing pocket depth (PPD; current periodontal health) and clinical attachment level (CAL; cumulative destruction). PPD, CAL, and other clinical parameters form the basis of periodontal diagnosis. Radiography offers excellent sensitivity to hard tissue (bone, enamel, etc.) but cannot discriminate between healthy and diseased gingiva or map disease within soft tissue; it also has a small but non-negligible dose of ionizing radiation. Ultrasound imaging has the benefits of being a portable and low-cost alternative to radiography that is noninvasive and free of ionizing radiation. It can also resolve oral soft tissues including the gingiva and mucosa.

Locating the cementoenamel junction (CEJ) is important for determining metrics of periodontal health such as gingival recession and CAL. The CEJ is typically covered by the gingiva (subgingival), and its exact location is difficult to determine via physical probing and subject to significant error: In midbuccal sites, Vandana et al. reported over- or underestimation of the CEJ by trained periodontists for 74% (34/46) of measured teeth. Ultrasound recently been used to directly image and identify the CEJ and other dental and periodontal structures. Indeed, a rapidly expanding body of evidence has shown the translational value of ultrasonography for intraoral and dento-periodontal applications. To briefly summarize, a variety of clinically relevant anatomical features have been visualized including the alveolar bone, CEJ, gingival thickness, greater palatine foramen, lingual nerve, and oral mucosa in healthy humans, ex vivo swine jaws, and cadavers. Other reports have described computational approaches (e.g., machine and deep learning) to automatically extract these features from imaging data. Progress is also underway for improving the form factor and usability of transducer hardware and coupling materials. However, ultrasonographic studies that incorporate orally diseased subjects are relatively nascent. Two recent examples include the use of power and color Doppler ultrasonography for measuring tissue perfusion/inflammation at dental implant sites and soft tissue grafts. In a pilot study, Tattan et al. reported strong agreement between ultrasound and direct/cone-beam computed tomography measurements of periodontal dimensions in a cohort of periodontally healthy subjects with a 24-MHz transducer.

SUMMARY

High-frequency ultrasound was used for measuring critical metrics of periodontal health, including probing pocket depth, clinical attachment level, gingival recession, and gingival thickness at mid-labial sites. Image-based measurements of gingival height extended from the gingival margin to the alveolar bone crest and were comparable to probing pocket depth with functional equivalence for assessing disease status. Identification of the cementoenamel junction by human operators also allowed image-based measurement of alveolar bone level and gingival recession. Interexaminer bias was negligible (<0.1 mm) for gingival height and 0.45 mm for alveolar bone level measurements. Image-based alveolar bone level measurements were equivalent to clinical attachment level for staging disease. Overall, ultrasonographic metrics had at least an equivalent diagnostic capacity to gold-standard physical probing while offering more detailed anatomical information and painless operation.

In one aspect, a method is presented for measuring periodontal disease and treating diseases associated therewith. The method includes: obtaining B-mode ultrasound images of a dentition and periodontium of a patient; identifying gingival margin (GM), alveolar bone crest (ABC), cementoenamel junction (CEJ), periodontal ligament (PDL), and gingival edge (GE) biomarkers on the B-mode ultrasound images, the GE biomarker being a part of periodontal soft tissue most distal from a tooth surface; evaluating a metric associated with periodontal disease using one or more of the GM, ABC, CEJ, PDL and GE biomarkers and based at least in part on the evaluating, performing an act that implements and/or adjusts a therapeutic treatment of a periodontal disease.

In another aspect, a method is presented for measuring gingival thickness (GT) and treating diseases associated therewith. The method includes: obtaining B-mode ultrasound images of dentition and periodontium of a patient; identifying GE, ABC, and GM biomarkers on the B-mode ultrasound images; determining a first distance between the ABC and GM biomarkers; determining a facial midpoint along the first distance; determining a second distance between the facial midpoint and the GE biomarker to define an imaged-based metric associated with gingival thickness (GT); evaluating the image-based metric associated with GT; and based at least in part on the evaluation of the image-based metric, performing an act that implements and/or adjusts a therapeutic treatment of a periodontal disease. In some cases the act that implements and/or adjusts a therapeutic treatment of a periodontal disease includes a gum flat transplant.

In yet another aspect, a method is presented for measuring gingival recession (GR) and treating diseases associated therewith. The method includes: obtaining B-mode ultrasound images of a dentition and periodontium of a patient; identifying CEJ and GM biomarkers on the B-mode ultrasound images; determining a distance between the CEJ and GM biomarkers along a plane parallel to a tooth surface defining an image-based gingival recession (iGR) metric associated with recession; evaluating the IGR metric; and based at least in part on the evaluation of the iGR metric, performing an act that implements and/or adjusts a therapeutic treatment of a periodontal disease. In some cases the act that implements and/or adjusts a therapeutic treatment of a periodontal disease includes a gum flat transplant or scalar root planing.

In another aspect, a method is presented for measuring a surrogate of periodontal pocket depth and treating diseases associated therewith. The method includes: obtaining B-mode ultrasound images of a dentition and periodontium of a patient; identifying ABC and GM biomarkers on the B-mode ultrasound images; determining a distance between the ABC and GM biomarkers defining an image-based gingival height (iGH) metric; and based at least in part on the evaluation of the iGH metric, performing an act that implements and/or adjusts a therapeutic treatment of a periodontal disease. In some cases the act that implements and/or adjusts a therapeutic treatment of a periodontal disease includes a gum flat transplant or scalar root planing.

In another aspect, a method is presented for measuring a surrogate of clinical attachment loss and treating diseases associated therewith. The method includes: obtaining B-mode ultrasound images of a dentition and periodontium of a patient; identifying ABC and CEJ biomarkers on the B-mode ultrasound images; determining a distance from the ABC biomarker to the CEJ biomarker to define an image-based alveolar bone level (iABL) metric; evaluating the iABL metric; and based at least in part on the evaluation of the iABL metric, performing an act that implements and/or adjusts a therapeutic treatment of a periodontal disease. In some cases the act that implements and/or adjusts a therapeutic treatment of a periodontal disease includes a gum flat transplant or scalar root planing.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTION OF THE DRAWINGS

FIG. 2G compares ultrasound (US) measurements and physical (tactile) probing measurements by a periodontist.

4

DETAILED DESCRIPTION

Figure 1A:
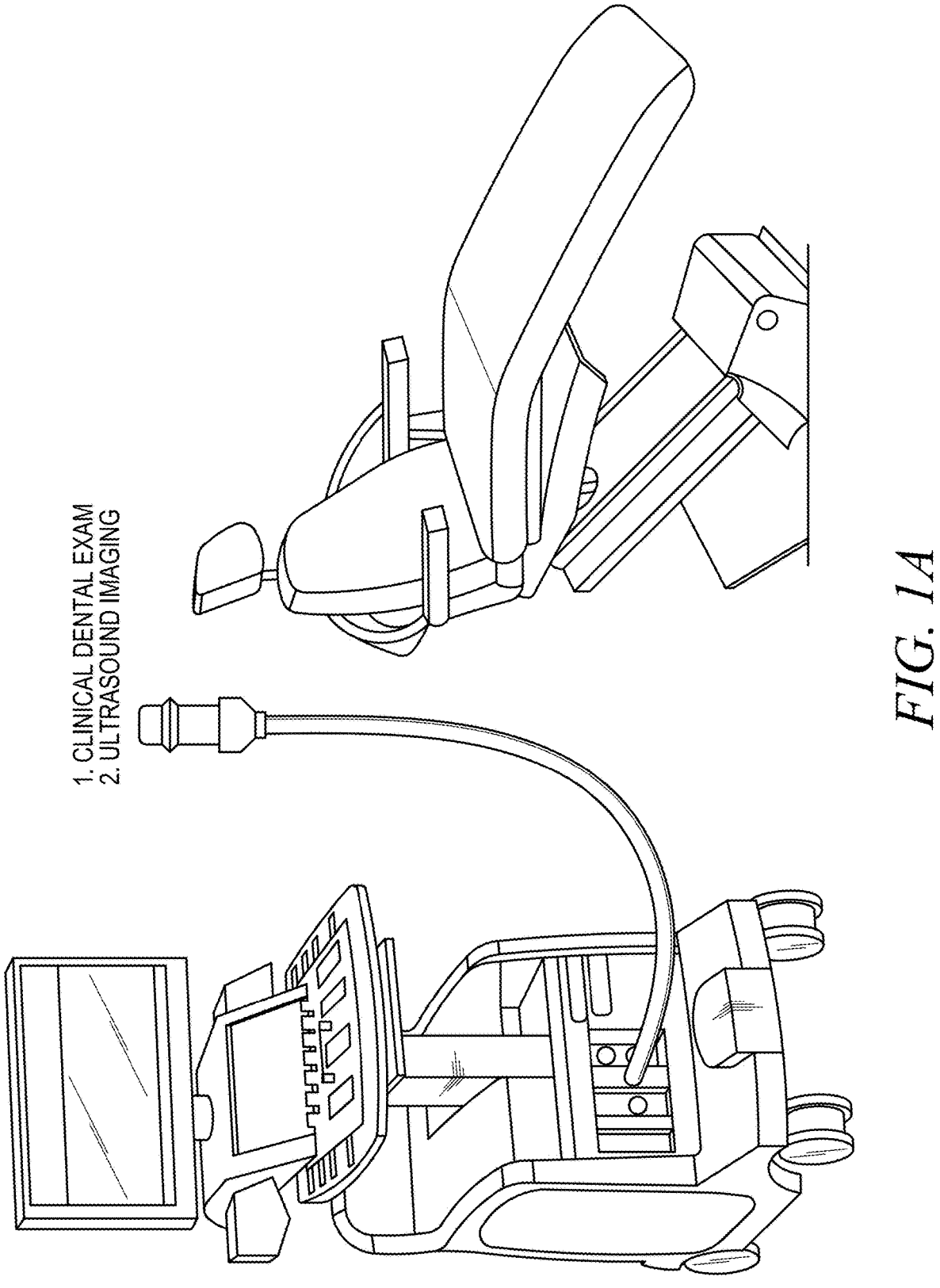
FIGS. 1A-1E provide an overview of periodontal ultrasound imaging.

Described herein are systems and methods in which high-frequency (e.g., 40-MHz) ultrasound is used to locate the CEJ in relation to other anatomical biomarkers (e.g., the gingival margin (GM) and alveolar bone crest (ABC)) for image-based determinations of periodontal metrics in periodontally healthy and diseased subjects. We compared these biomarkers to established clinical metrics of periodontal health. Ultrasonographic imaging measurements is shown to serve as a surrogate for clinical probing, providing an ultrasonographic determination of periodontal metrics in both healthy and diseased subjects for comparison with tandem clinical diagnosis.

Materials & Methods

The systems and methods described will be described using specific materials, techniques and a select group of subjects which are presented for illustrative purposes only and not as a limitation on the systems and method described herein. The manner in which these subject were selected and the specific materials and techniques used will now be described.

A high-frequency, commercially available imaging ultrasound system was employed (Vevo 2100/LAZR, Visualsonics, Toronto CA) using a linear array transducer (LZ-550, Fc=40 MHz) with spatial resolution <200 μm. Disposable tegaderm films were used as sterile transducer sleeves (3M, Minnesota, USA). Periodontal probing measurements were conducted with a Williams and Marquis probe. Extracted swine jaws were provided by Sierra For Medical Science, Inc. (Whittier, CA). Of course, those of ordinary skill will recognize that more generally any suitable imaging ultrasound system may be employed.

The study protocol was approved by the USC and UCSD Institutional Review Boards and was in accordance with the ethical guidelines for human subjects research established by the Helsinki Declaration of 1975. The study subjects were identified from patients seeking dental care at the Herman Ostrow School of Dentistry. As part of the clinical protocol, the patients received extra- and intra-oral examinations, medical and dental history review, a set of full-mouth radiographs, periodontal examination, periodontal diagnosis, and treatment planning. Eligible subjects were healthy adults who weighed at least 110 pounds with one quadrant with at least upper and lower anterior teeth. Subjects were excluded if they had bloodborne pathogen infections, bleeding disorders, acute oral infections, or were pregnant or lactating women. Two subject groups were recruited based on the periodontal diagnosis described in the 2017 World Workshop on the Classification of Periodontal and Peri-implant Diseases and Conditions. The first group (n=10) comprised subjects with the following diagnosis: periodontal health in intact or reduced periodontium in stable periodontitis patients, or dental biofilm-induced gingivitis in the intact or reduced periodontium. The second group (n=6) comprised subjects diagnosed with periodontitis (Stage II-IV and Grade B or C) with localized or generalized involvement.

The periodontal diagnosis was given by a board-certified periodontist faculty and a resident. Six maxillary or mandibular anterior teeth were then selected for the study. We could not access molars because of the size of the transducer. Periodontal probing depth was determined with a Williams and Marquis probe at six sites per tooth (mesio-labial, mid-labial, disto-labial, mesio-lingual, mid-lingual, and disto-lingual). Tooth mobility was determined as Class 1: mobility of up to 1 mm in an axial direction, Class 2: mobility of greater than 1 mm in an axial direction, and Class 3: mobility in an apico-coronal direction (depressible tooth). Bleeding on probing (BOP) provoked by applying a probe to the bottom of the sulcus/pocket was recorded. Gingival recession was recorded by measuring the distance between the CEJ to the top of the gingival margin (GM) at the mid-labial position of the tooth with a periodontal probe. CAL was determined from the CEJ to the bottom of the sulcus. The gingival phenotype was determined by inserting the periodontal probe at the mid-labial sulcus of the tooth. A thin gingival phenotype was assigned if the probe was visible through the gingival tissue according to clinical convention.

Figure 1B:
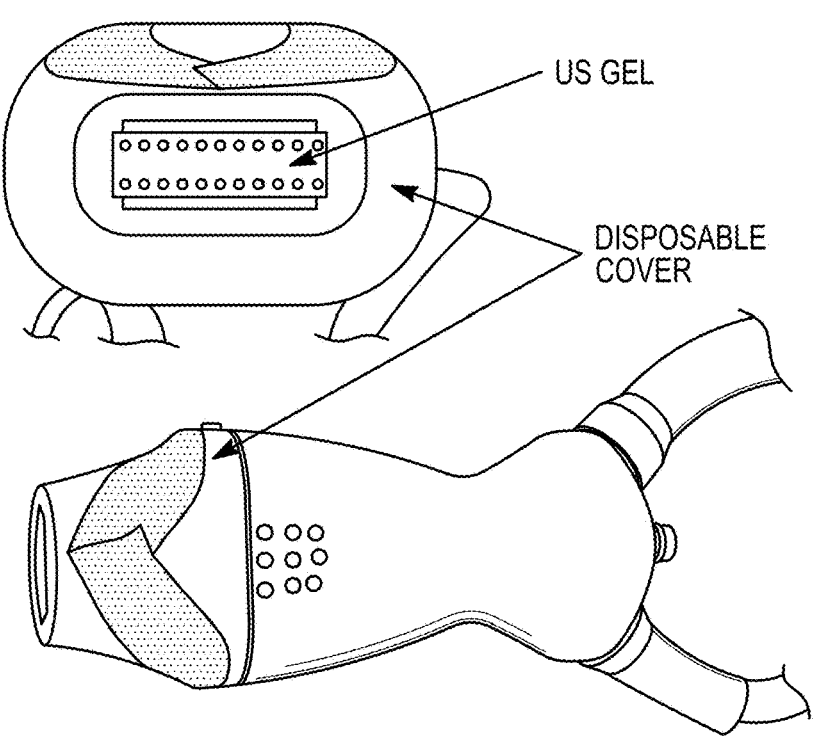
Figure 1C:
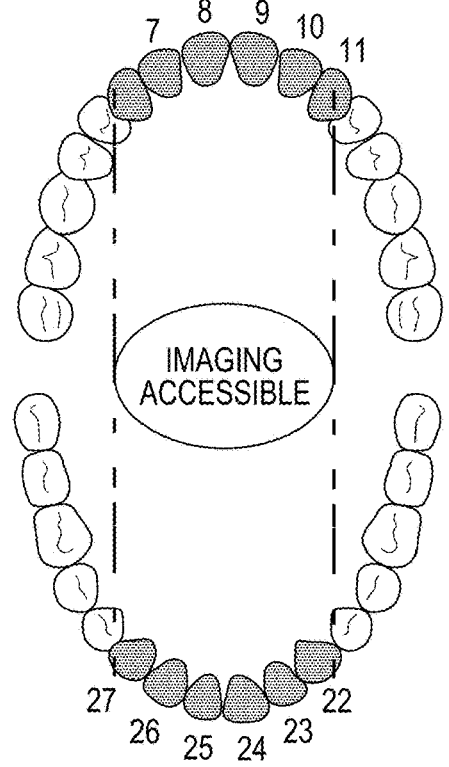

FIG. 1A shows a schematic of a high-frequency, commercially available imaging system that was used for chairside imaging of subjects. Subjects were seated in the supine position in a dental chair and imaged by a clinician with a handheld, linear array transducer. A disposable sleeve was used to wrap the transducer in addition to sterile ultrasound coupling gel. Imaging was performed manually by positioning the transducer parallel to the long axis of the tooth along the labial midline. FIG. 1B shows a photograph of the handheld linear array transducer with the coupling gel and sterile sleeve, which permitted access to the maxillary/mandibular incisors and cuspids (teeth 6-11 and 22-27). FIG. 1C shows a dental chart with teeth highlighted (6-11, 22-27) that could be physically accessed by the transducer. B-mode images (2D ultrasound cross-sectional images) were collected in the sagittal plane at the mid-labial site of each tooth.

Figure 1D:
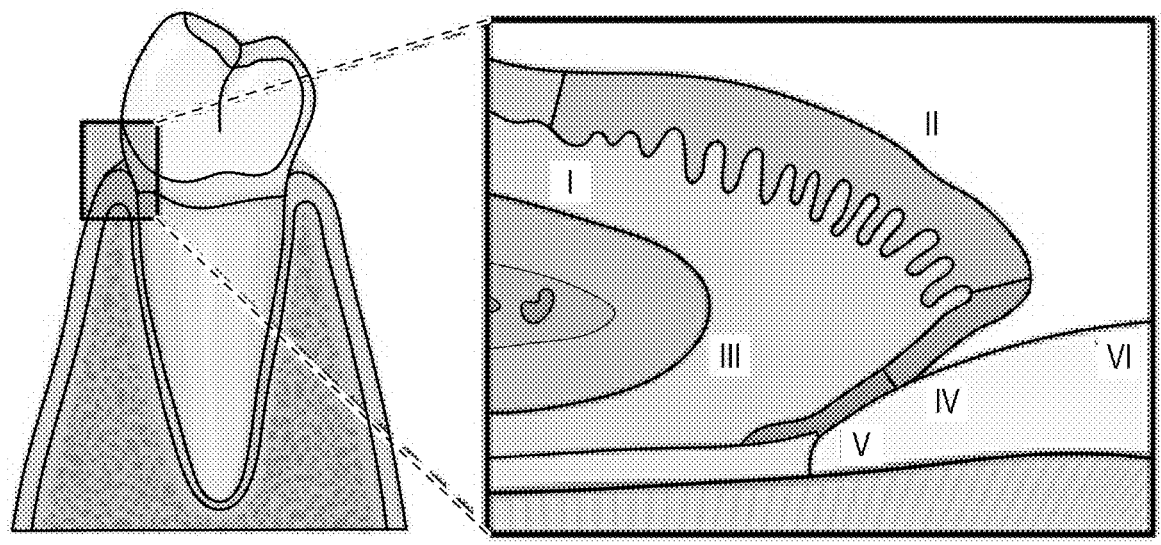
Figure 1E:
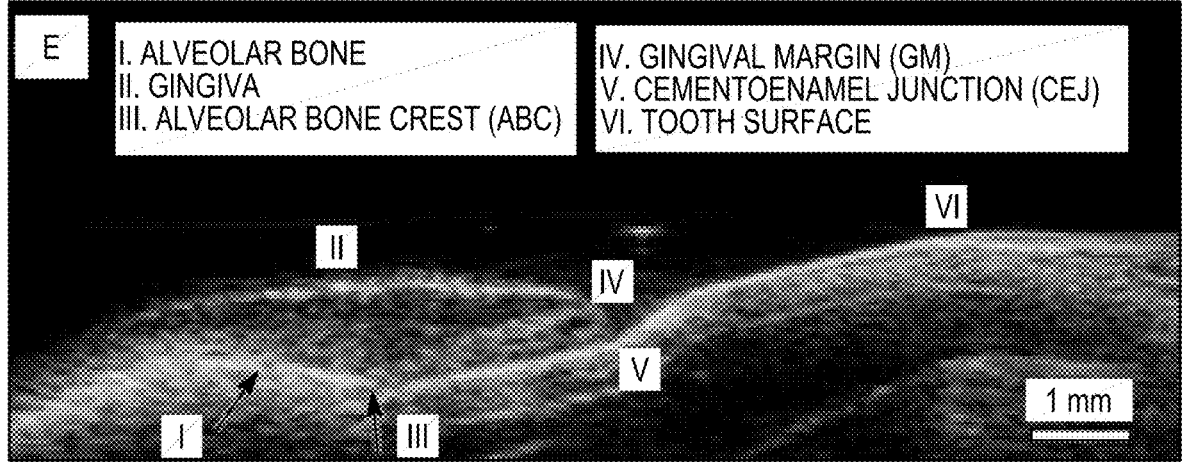

The anatomy of the imaged region is depicted in FIG. 1D for comparison to a representative B-mode image in FIG. 1E. In particular, FIG. 1D shows a diagram of the periodontal anatomy surrounding the gingival sulcus with magnification of the sagittal plane. Roman numerals denote the I: alveolar bone, II: gingiva, III: alveolar bone crest (ABC), IV: gingival margin (GM), V: cementoenamel (CEJ), VI: tooth surface. FIG. 1(D) shows B-mode ultra sound image of the region in FIG. 1(C) for the central mandibular incisor (#25) of a patient with anatomical markers labeled. In general, six anatomical markers were consistently identified and used to orient the imaging operator: the alveolar bone, the gingiva, ABC, GM, CEJ, and the tooth surface.

Images were analyzed and measured manually. All images had to meet specific quality criteria by the examiner prior to measurement. These were: 1) identification of the GM, (2) identification of the ABC, and (3) a lack of interfering artifacts coincident with the relevant anatomy. If these conditions were met, then further image analysis was performed (Table 1). All imaging measurements were performed in duplicate by two blinded examiners and averaged. The first was a clinician with no ultrasound experience (Examiner 1) while the second was an ultrasound researcher with no clinical experience (Examiner 2). Imaging measurements were performed digitally by each examiner in the VisualSonics software and ImageJ. The distance from the GM to the ABC was defined as the image-based gingival height (iGH). Similarly, the distance from the CEJ to the ABC was defined as the image-based alveolar bone level (iABL). The image-based gingival thickness (iGT) was measured at the midpoint of the ABC and GM.

Figure 5:
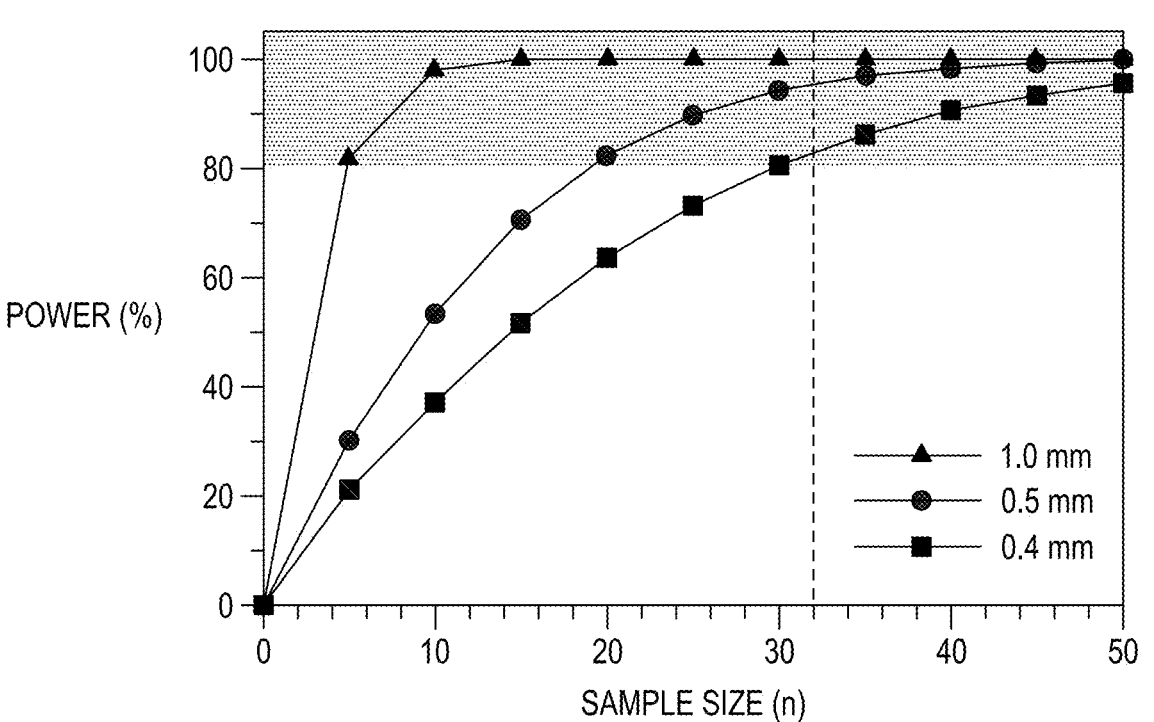
FIG. 5 shows statistical power as a function of group sample size (number of imaged/measured teeth) with three different effect sizes.

The suitability of sample size for determining measurement differences between teeth grouped as periodontally healthy or diseased was estimated via power analysis for a two-tailed significance test with 95% significance (alpha=0.05), 80% power (beta=0.20), variance=0.3 mm$^2$, and minimum differences of 0.4, 0.5, or 1.0 mm. FIG. 5 shows statistical power as a function of group sample size (number of imaged/measured teeth) with three different effect sizes. Statistical power was calculated for a two-tailed significance test with $\alpha$=0.05, $\beta$=0.20, and $\sigma^2$=0.3 mm$^2$ for minimum differences of 0.4 mm (blue), 0.5 mm (green), and 1.0 mm (red). The gray region represents sample size values with sufficiently high power (>80% by convention) for each minimum difference curve. The dotted line shows the diseased group sample size in this study (n=32), demonstrating sufficient power for detecting a minimum significant difference of ≥0.4 mm.

Bland-Altman analysis was performed to quantify differences (bias, limits of agreement) between image analysts and between physical probing and imaging measurements. Box-and-whisker plots were combined with unpaired, two-tailed significance testing (alpha=0.05) to compare healthy and diseased groups of measured/imaged teeth. Analysis was performed with GraphPad Prism 9 (San Diego, CA) and Microsoft Excel (Redmond, Washington).

Results

In humans, 79 B-mode images were acquired from 16 subjects comprising 43 teeth clinically diagnosed as healthy and 36 diagnosed with periodontal disease via physical measurements and examination. Of these images, 66 (84%) met quality criteria and were used for analysis. All image quality metrics, image measurements, and clinical measurements are included in Table 1.

Figures 2A, 2B, 2C, 2D, 2E, 2F:
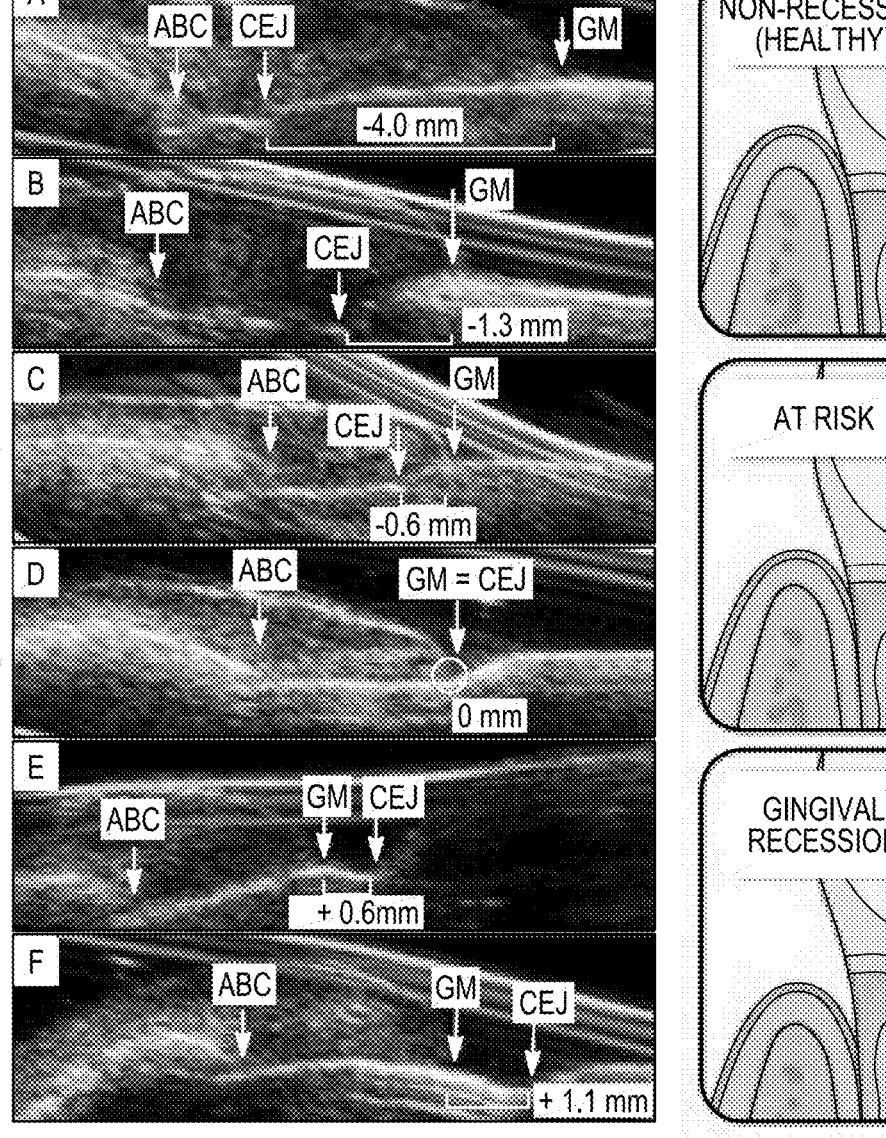
FIGS. 2A-2F show B-mode images in six subjects demonstrating ultrasound (US) monitoring of gingival recession via periodontal landmarks.

One simple periodontal measurement is the distance between the CEJ and GM, which is used to assess gingival migration (recession or overgrowth). To demonstrate this with ultrasonography, FIG. 2 shows varying positions of the CEJ relative to the GM for six different subjects. In particular, FIGS. 2A-2F show teeth from subjects with increasing levels of gingival recession. FIGS. 2A-2C show images from subjects with the CEJ apical to the GM (i.e., non-recessed).

The CEJ presents as an angled disruption in the echogenicity of the tooth surface between the GM and ABC. For subjects in FIGS. 2A-2C, the CEJ is apical to the GM (typically, a positive health marker) showing subgingival CEJ-GM distances of −4.0 mm, −1.3 mm, and −0.6 mm. The CEJ and GM are coincident in FIG. 2D. The last two cases have gingival recession (FIGS. 2E-2F): The GM is apical to the CEJ (0.6 mm and 1.1 mm respectively). FIG. 2G compares ultrasound (US) measurements and physical (tactile) probing measurements by a periodontist.

Figure 3A:
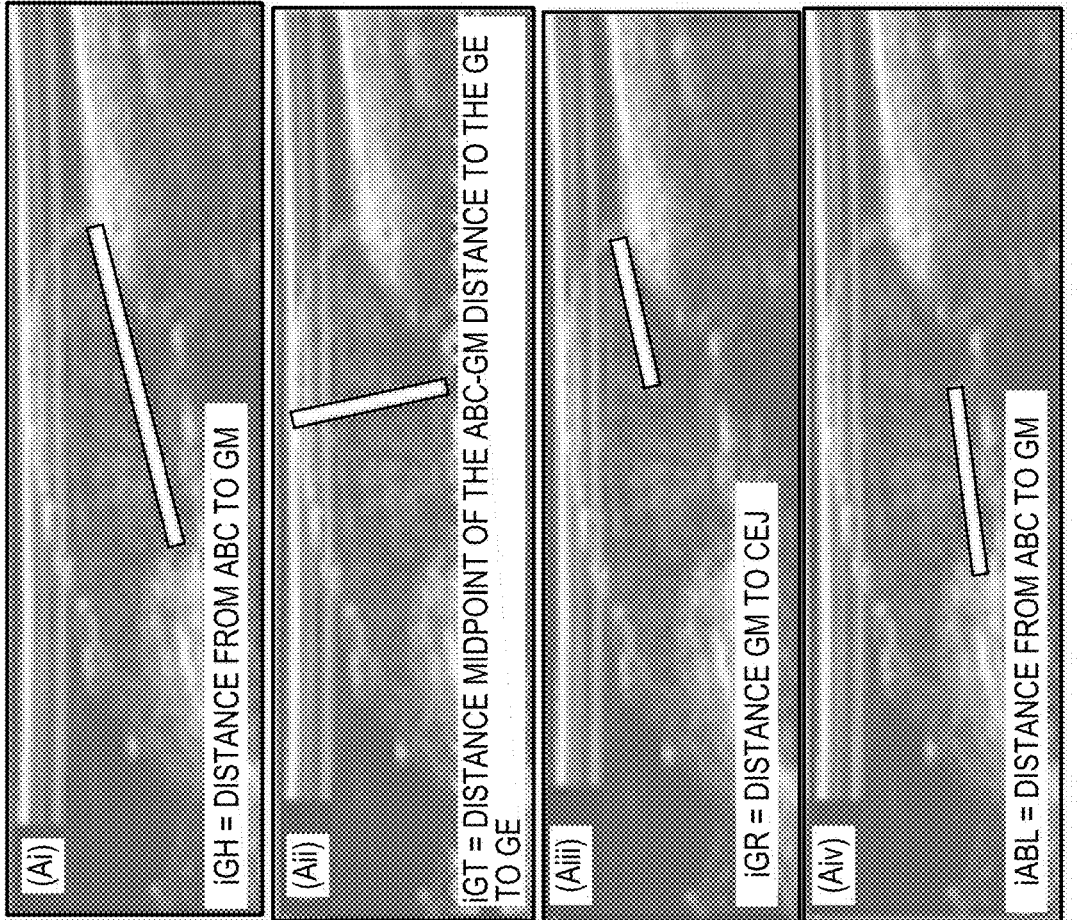
FIGS. 3A-3C show ultrasound images for diagnostic measurements and interrater variability data for US image-based measurements of pocket depth (iPD) and clinical attachment level (iCAL).
Figure 3B:
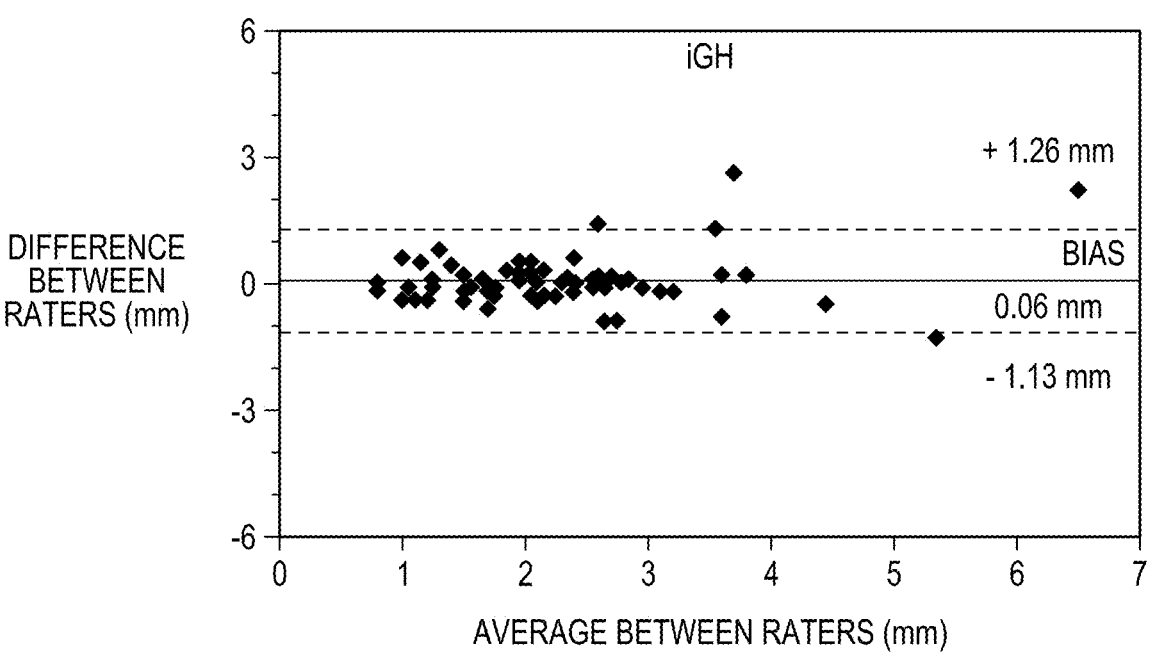
Figure 3C:
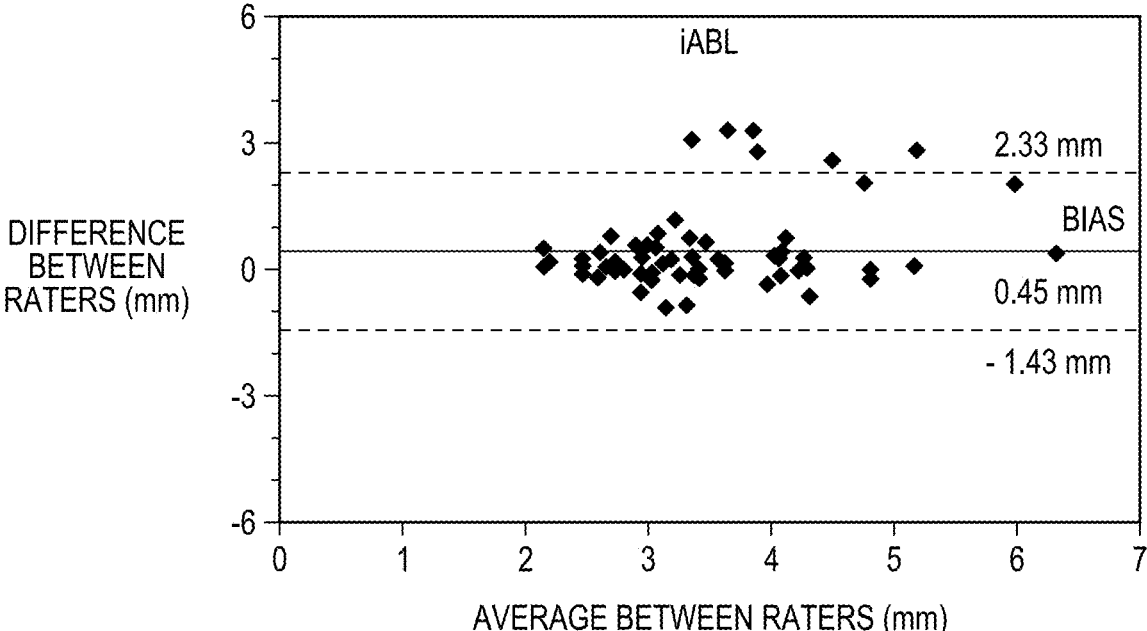

All image-based measurements including iGH, iABL, iGT, and iGR (image-based gingival recession), are depicted for a representative tooth site in FIG. 3A. Panels Ai, Aii, Aiii, and Aiv expand on FIG. 3A and further illustrate the imaging biomarkers iGH, iGT, iGR, and iABL. The iGH biomarker is measured from the ABC to the GM. To determine the iGH and iABL values in this study, two blinded examiners independently measured each B-mode image and their values were averaged. FIGS. 3B-3C show Bland-Altman plots comparing the iGH and iABL measurements from two blinded image analysts for the same image set (n=66 teeth). Bias between raters was <0.1 mm for iGH (FIG. 3B) and 0.45 mm for iABL (FIG. 3C).

Figure 4A:
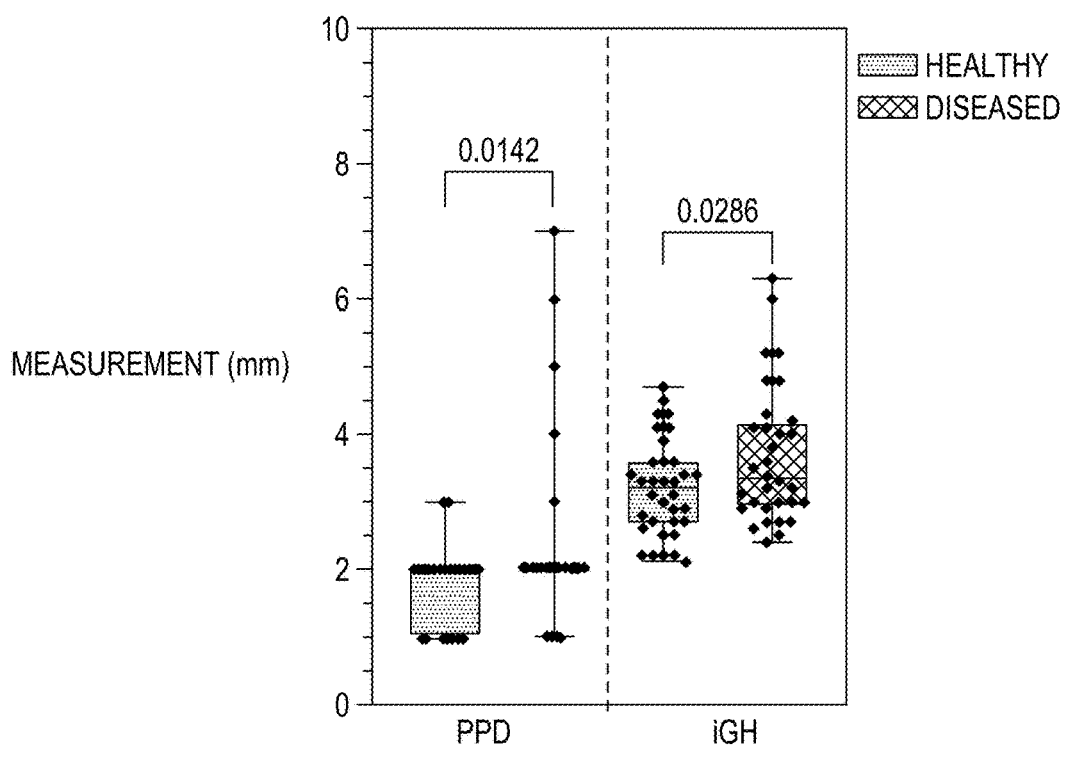
FIGS. 4A-4D compare US image-based measurements (iGH, iABL) and clinical probing measurements (PPD, CAL) for individual teeth (n=66) of patients with healthy or diseased clinical diagnoses.

The average iGH and iABL values for teeth from healthy/diseased subjects were compared to clinical PPD and CAL measurements, respectively. FIG. 4 shows a comparison between US image-based measurements (iGH, iABL) and clinical probing measurements (PPD, CAL) for individual teeth (n=66) of patients with healthy or diseased clinical diagnoses. In particular, FIG. 4A shows box-and-whisker plots for PPD and iGH, which both indicate significantly higher measurements in the diseased group (n=32) than the healthy group (n=34). PPD values are limited to integers. Pairwise comparison values are p-values (unpaired t-test). The average PPD measurements were 1.68 mm for healthy subjects and 2.25 mm for diseased subjects. A similar increase was observed for iGH measurements: 3.19 mm for healthy subjects and 3.67 mm for diseased subjects. In both cases, measurements in diseased subjects were significantly higher than in healthy subjects (unpaired, two-tailed t-test, p=0.0142 for PPD, p=0.0286 for iGH).

Figure 4B:
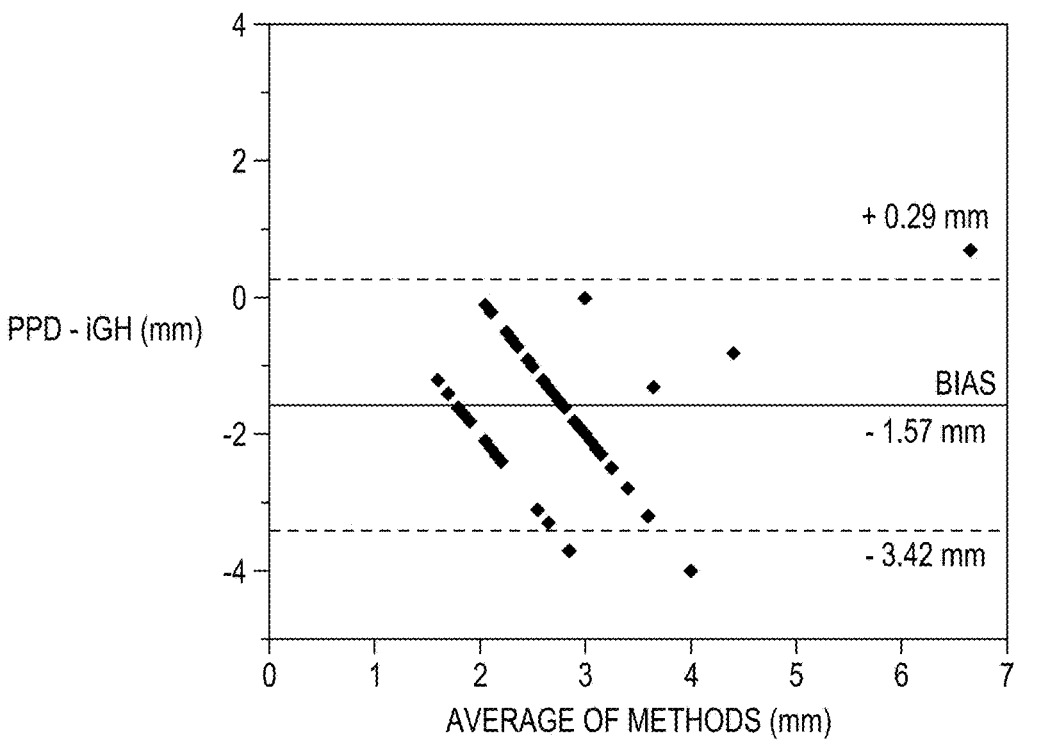
Figure 4C:
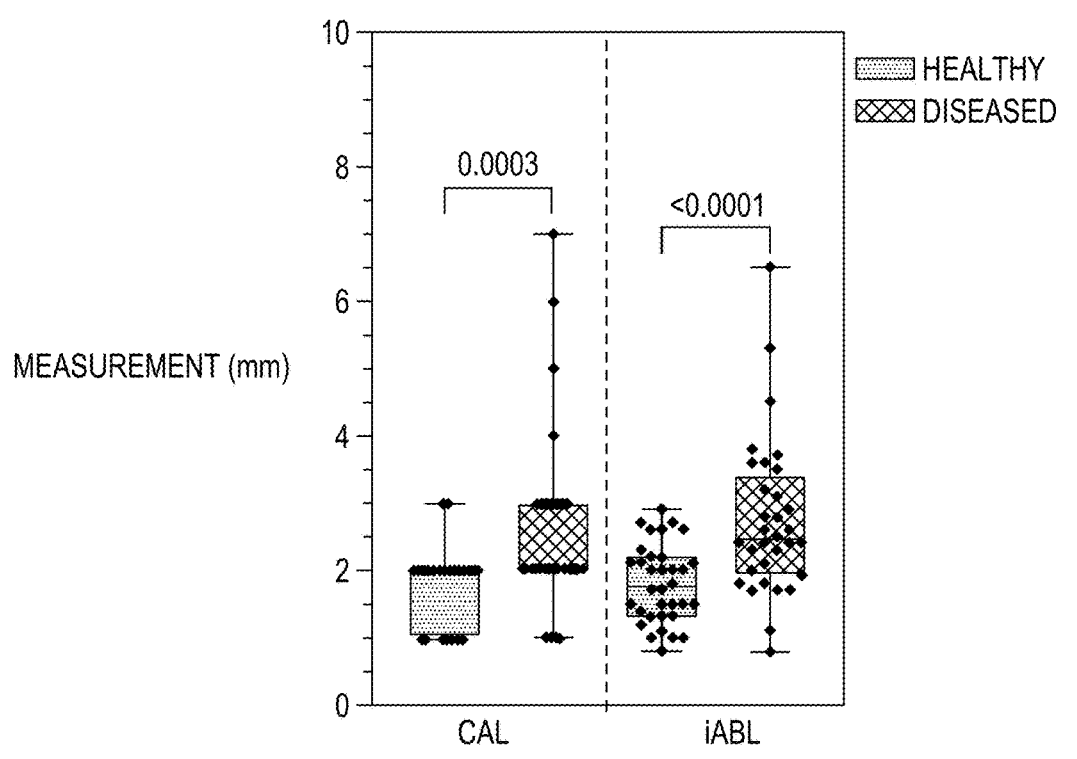
Figure 4D:
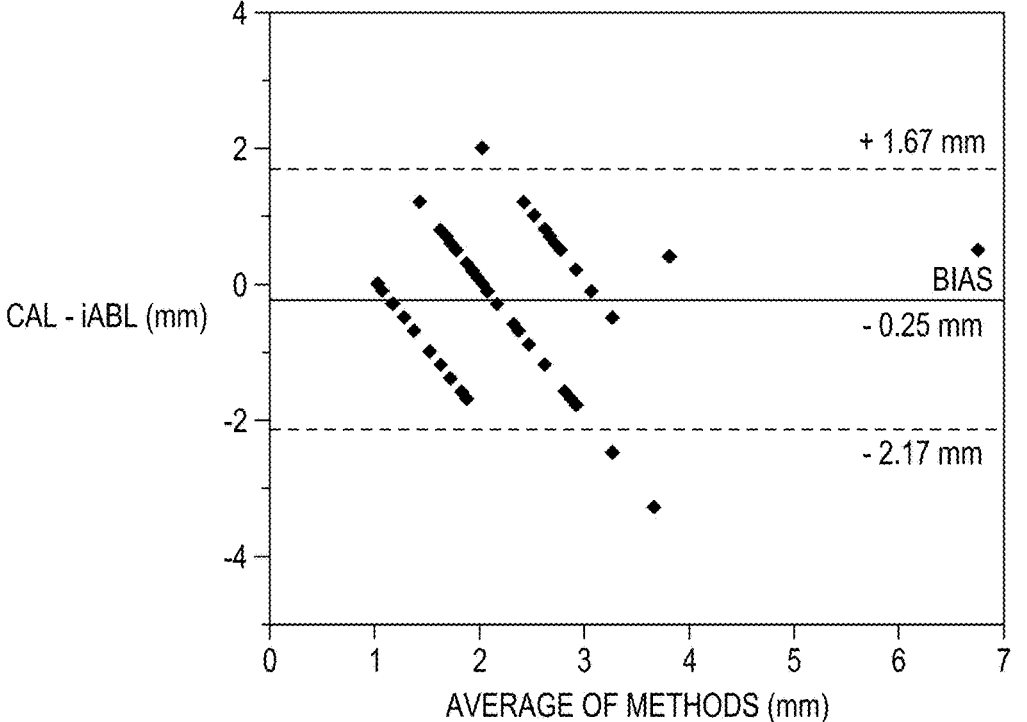

FIG. 4B shows a Bland-Altman analysis between the measurement methods, which reveal a 1.57±0.95 mm bias toward iGH measurements averaged from all teeth—these values are larger because though both measurements begin at the GM, the iGH is measured to the ABC rather than the terminus of the gingival sulcus. This difference, due to the connective tissue and junctional epithelium between the ABC and gingival sulcus, is referred to as the biological width. FIG. 4C shows box-and-whisker plots for iABL and CAL, which indicate significantly higher values for teeth in the diseased group than the healthy group (1.68 mm in the healthy group and 2.56 mm in the diseased group). CAL values are limited to integers. Pairwise comparison values are p-values (unpaired t-test). For iABL, the healthy average was 1.80 mm, and the diseased average was 2.74 mm—this difference between groups was even more significant than the CAL measurements (p<0.0001, FIG. 4C. FIG. 4D shows a Bland-Altman analysis between the iABL/CAL measurement methods, which reveal a 0.25±0.98 mm bias toward the iABL measurements, indicating a minimal difference between the two methods. Overall, the average increases in magnitude of PPD, iGH, CAL, and iABL for diseased versus healthy teeth were 34%, 15%, 52%, and 52%, respectively.

Figure 6A:
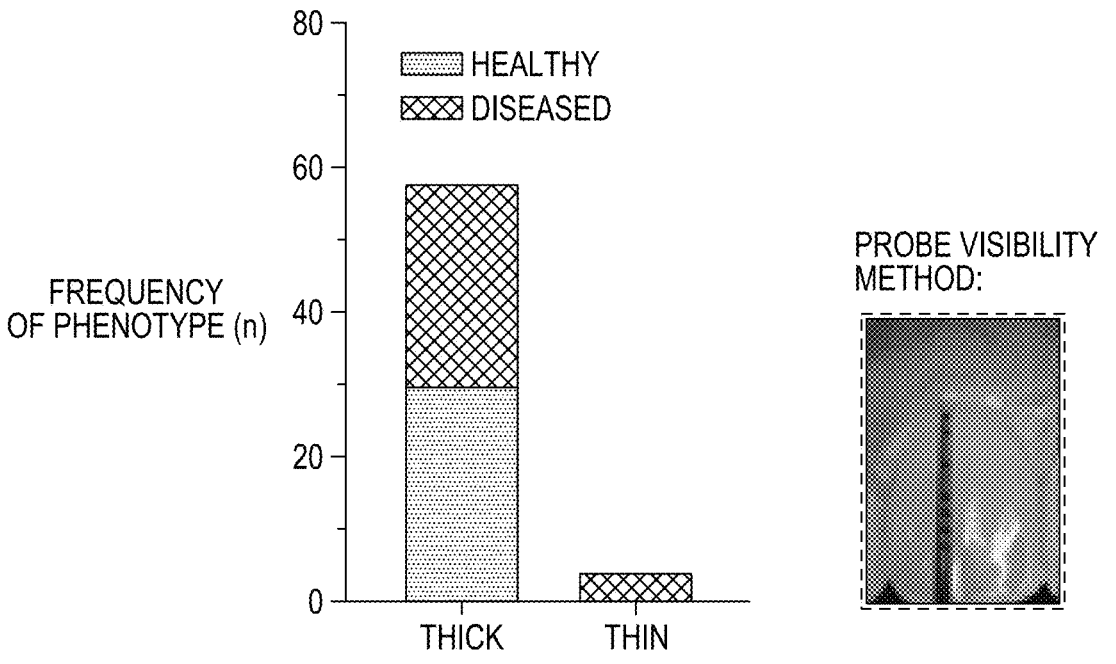
FIG. 6A-6B shows a comparison between clinically assigned biotype and US image-based measurements of gingival thickness (iGT).
Figure 6B:
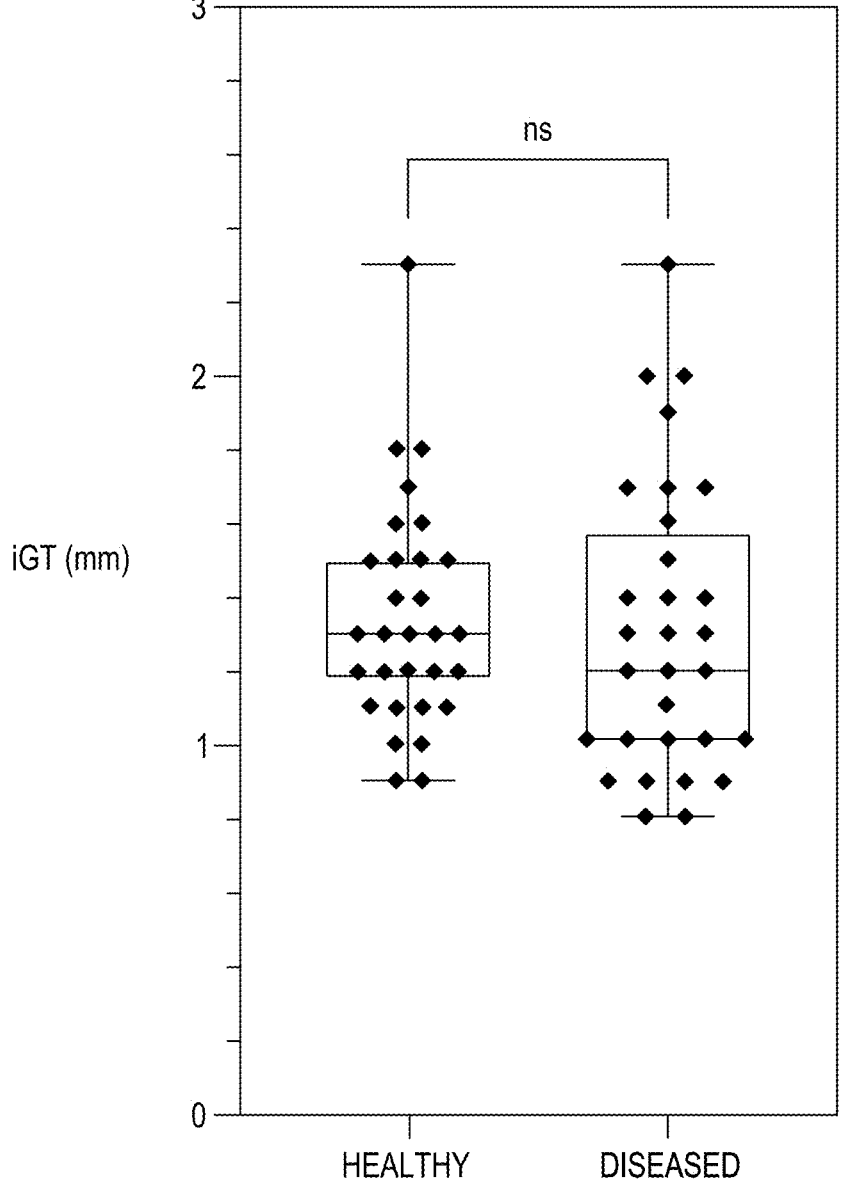

In our dataset, the average difference between iGH and PPD measurements was 1.57 mm. Defining this value as the average biologic width and subtracting it from each iGH measurement, we obtained a set of iPD values after rounding to the nearest integer similar to the rounding done when measuring the PPD. Likewise, we obtained a set of iCAL values after performing the same subtraction from the iABL data. This analysis led to 83% agreement between iPD and PPD values, and 49% agreement between iCAL and CAL values; here, agreement was defined as ≤1 mm difference between paired measurements. Lastly, iGT was compared to gingival biotype: 93.5% of the associated gingiva for measured teeth possessed a thick biotype, and there was no correlation to disease status. FIGS. 6A and 6B show a comparison between clinically assigned biotype and US image-based measurements of gingival thickness (iGT). In particular, FIG. 6A shows teeth from healthy and diseased groups being classified as a thick or thin biotype according to the conventional probe-visibility method. (Photographic inset: example of a thick biotype). FIG. 6B shows that the imaged gingival thickness (iGT) can provide significantly more quantitative assessment (<0.1 mm precision over the full cross-sectional area) than probe-based biotyping. As expected, no significant difference was observed between iGT for the healthy and diseased groups. Here, the iGT was measured from the midpoint between the ABC and GM.

Figure 7:
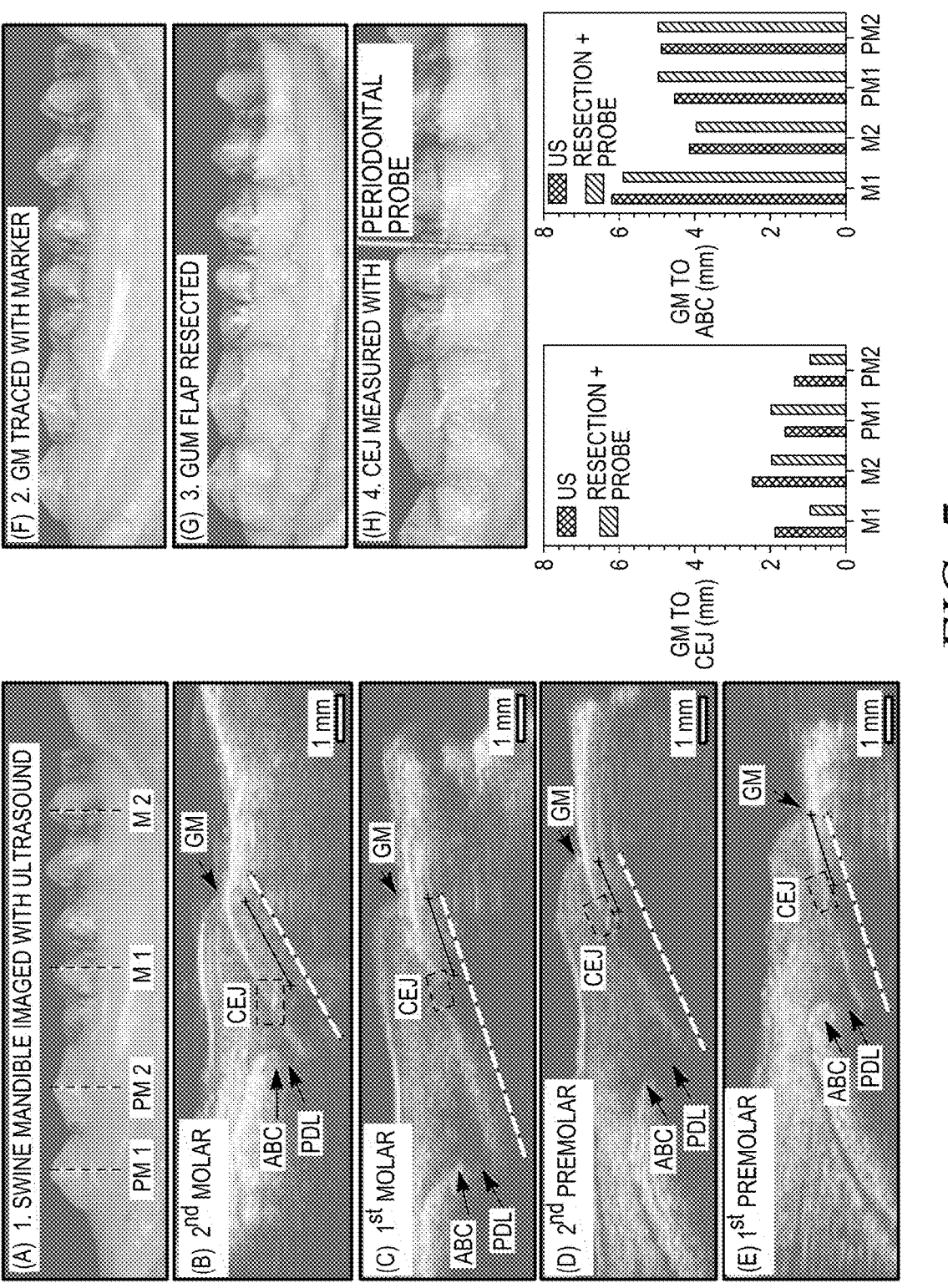
FIGS. 7A-7I show images and data comparing ultrasound to physical examination for an extracted swine mandible following gum flap resection and periodontal measurement with physical probing.

FIG. 7 shows images and data comparing ultrasound to physical examination for an extracted swine mandible following gum flap resection and periodontal measurement with physical probing. In particular, FIG. 7A is a photograph of the $2^{nd}$ molar (M2), $1^{st}$ molar (M1), $2^{nd}$ premolar (PM2), $1^{st}$ premolar (PM1), and the imaging plane for each tooth (thin white dashed lines). FIGS. 7B-7E show visualizations of the cementoenamel junction (CEJ) relative to the alveolar bone crest (ABC) and gingival margin (GM) for the $2^{nd}$ molar (FIG. 7B), $1^{st}$ molar (FIG. 7C), $2^{nd}$ premolar (FIG. 7D), and first premolar (FIG. 7E). The CEJ is consistently resolvable as a disruption in the echogenicity of the tooth surface between the GM and the ABC. The image-based measurements of the GM to CEJ (thin lines) were M2=2.48, M1=1.88, PM2=1.39 mm, PM1=1.60 mm. The corresponding GM to AC measurements (thick dashed lines) were M2=4.19 mm, M1=6.30 mm, PM2=4.95 mm, PM1=4.59 mm. As seen in FIG. 7F, following imaging, the GM was traced along the teeth with a marker. In FIG. 7G, the gingiva (gum flap) was resected to reveal the roots of the teeth. In FIG. 7H the distances from GM to CEJ and GM to ABC were measured by a clinician using physical probing. The values in FIG. 7I were plotted and compared to the image-based measurements (<1.0 mm difference between GM-CEJ values (mean percent difference=34%) and <0.5 mm difference between GM-ABC values (mean percent difference=4.8%)). All resection+probe values were restricted to integers.

Discussion

The CEJ and the GM are two of the most prominent features in ultrasound images at mid-labial sites (FIG. 1E). These can be used to precisely measure the extent of gingival recession or overgrowth (FIG. 2), which is otherwise an error-prone estimate using periodontal probing. We envision that the ability to resolve the CEJ quickly and objectively in relation to the GM using chairside and hand-held transducers will enable more accurate and higher throughput longitudinal monitoring of gingival recession than standard probing. Of course, gingival recession alone does not provide a full picture of periodontal health because it is often multifactorial in origin. Therefore, we investigated the value of measurements derived from the CEJ, GM, and ABC as diagnostic gingival biomarkers, i.e., iGH and iABL (FIG. 3A). Interexaminer bias values from Bland-Altman analysis were acceptably low for both iGH (0.06 mm) and iABL (0.45 mm) (FIG. 3B-C) because these are lower than the precision of clinical probing which is restricted to integer measurements. The increased difference for iABL arose from differences between the examiners in assigning the CEJ, which can be a less obvious feature than the ABC or GM.

We found that sonography alone-even at high frequency (40 MHz in this study)-cannot resolve the periodontal pocket or depth of the gingival sulcus directly via endogenous contrast. This is likely because the free (unattached) gingiva that forms the sulcus remains conformal with the tooth surface, thus rendering it indistinguishable via endogenous imaging from attached gingiva. Nevertheless, iGH and iABL were effective surrogate measurements for PPD and CAL as illustrated by their similarly increased magnitudes for periodontally diseased vs. healthy teeth (FIG. 4). We compared iGH to PPD and iABL to CAL because these measurements are physically equivalent except for their termini—i.e., the iGH and iABL terminate at the ABC while the PPD and CAL terminate at the apex of the gingival sulcus. This difference—the distance between the ABC and the terminus of the gingival sulcus (corresponding to connective tissue and junctional epithelium)—has been described as the "biologic width". While our measured estimate for the biologic width (1.57 mm) falls within the range of mean values reported in a systematic meta-analysis (between 1.15-3.95 mm), the disease state, tooth type, probing depth, and attachment loss can all of course affect the biological width. The combination of these variables and the lack of precision in locating the subgingival CEJ with a periodontal probe are likely reasons for the relatively low agreement between iCAL and CAL values in this study (49%). Given the higher accuracy of physical probing for PPD measurements, the comparison between iPD and PPD is both more reliable and promising with 83% agreement. Importantly, while recapitulating the PPD values via imaging has value, the iGH and iABL are simpler metrics and do not require a priori estimation of the biologic width. Treating the biologic width as a correction factor is useful to help correlate these gingival biomarkers to conventional metrics of periodontal health; however, it is possible to imagine them being used independent of conventional probing measurements.

Ultrasound can also measure gingival thickness with a high degree of precision and accuracy—while iGT alone does not reflect periodontal health, it is an important metric in the context of operations such as gum grafts and periodontal flap surgeries. Currently, biotype is a binary evaluation performed by inserting the periodontal probe into the gingival sulcus and assessing probe visibility. A visible probe corresponds to a "thin" biotype and an invisible probe corresponds to a "thick" biotype. Actual values for thin and thick biotypes have been proposed as <1.0 mm GT and >1.0 mm GT, respectively. We did not observe a statistical difference between GT or iGT measurements in healthy and diseased patients (FIG. 6).

Though imaging is significantly more precise than the probe visibility method, this comparison served as assurance that iGT measurements were not biased by the health status of the patient.

The imaging technique faced a few limitations. Many images possessed reflection artifacts from the transducer sleeve. These artifacts were generated by the specific geometry of the transducer, i.e., the ~0.5-mm gap between the transducer elements and the tissue surface—fortunately, many transducers do not have this gap. Another limitation of the transducer was its size. This restricted imaging in the illustrative examples to the labial surfaces of teeth 6-11 and 22-27. The use of alternative transducers could access the buccal and lingual surfaces of the full dentition. Also, in some implementations of practical clinical systems computational techniques may employed to automatically extract imaging biomarkers. Nevertheless, ultrasound may have significant clinical value for longitudinal monitoring of periodontal health. Unlike other oral imaging modalities, ultrasonography offers details of both hard and soft tissues, thus facilitating the measurement of periodontal metrics that require the resolution of both hard (ABC, CEJ) and soft (GM, GT) features. It is non-ionizing, painless, and can be operated chairside with minimal training.

In summary, we investigated the use of high-frequency ultrasound in 10 healthy subjects (34 teeth) and 6 subjects with periodontal disease (32 teeth) for measuring critical metrics of periodontal health, including probing pocket depth, clinical attachment level, gingival recession, and gingival thickness at mid-labial sites. Image-based measurements of gingival height extended from the gingival margin to the alveolar bone crest and were comparable to probing pocket depth (1.57-mm magnitude bias) with functional equivalence for assessing disease status. Identification of the cementoenamel junction by human operators also allowed image-based measurement of alveolar bone level and gingival recession. Interexaminer bias was negligible (<0.1 mm) for gingival height and 0.45 mm for alveolar bone level measurements. Image-based alveolar bone level measurements were equivalent to clinical attachment level for staging disease (0.25-mm magnitude bias). Overall, ultrasonographic metrics had at least an equivalent diagnostic capacity to gold-standard physical probing while offering more detailed anatomical information and painless operation. We anticipate that advances in the form factor of high-frequency transducers will facilitate the further translation of ultrasonography into the dental clinic.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments.

TABLE 1

| | | | Image index and quality | | | | Clinical measurements | | |
| | | | | Free of | Image | | | | |
| Patient (n) | Clinical diagnosis | Tooth number | GM Identified? | ABC Identified? | interfering artifacts? | Quality (0-3) | Gingival Biotype | PPD (mm) | CAL (mm) |
|---|---|---|---|---|---|---|---|---|---|
| 1 | Healthy | 6 | X | ✓ | X | 1 | Thick | 3 | 3 |
| | | 7 | X | ✓ | X | 1 | Thick | 2 | 2 |
| | | 8 | ✓ | ✓ | ✓ | 3 | Thick | 2 | 2 |
| | | 9 | ✓ | ✓ | ✓ | 3 | Thick | 2 | 2 |
| | | 10 | ✓ | ✓ | ✓ | 3 | — | 1 | 1 |
| | | 11 | X | X | X | 0 | — | 1 | 1 |
| 2 | Healthy | 7 | ✓ | ✓ | ✓ | 3 | — | — | — |
| | | 8 | ✓ | ✓ | ✓ | 3 | — | — | — |
| | | 9 | ✓ | ✓ | ✓ | 3 | — | — | — |
| 3 | Healthy | 6 | ✓ | ✓ | ✓ | 3 | Thick | 1 | 1 |
| | | 7 | ✓ | X | X | 1 | Thick | 1 | 1 |
| | | 8 | ✓ | ✓ | ✓ | 3 | Thick | 2 | 2 |
| | | 9 | ✓ | ✓ | ✓ | 3 | Thick | 2 | 2 |
| | | 10 | ✓ | ✓ | ✓ | 3 | Thick | 2 | 2 |
| | | 11 | ✓ | ✓ | ✓ | 3 | Thick | 2 | 2 |

TABLE 1-continued

| | | | Image index and quality | | | | Clinical measurements | | |
|---|---|---|---|---|---|---|---|---|---|
| Patient (n) | Clinical diagnosis | Tooth number | GM Identified? | ABC Identified? | Free of interfering artifacts? | Image Quality (0-3) | Gingival Biotype | PPD (mm) | CAL (mm) |
| 4 | Healthy | 6 | ✓ | ✓ | ✓ | 3 | Thick | 1 | 1 |
| | | 7 | ✓ | ✓ | ✓ | 3 | Thick | 2 | 2 |
| | | 8 | ✓ | ✓ | ✓ | 3 | Thick | 2 | 2 |
| | | 9 | ✓ | ✓ | ✓ | 3 | Thick | 2 | 2 |
| | | 10 | ✓ | ✓ | ✓ | 3 | Thick | 2 | 2 |
| | | 11 | ✓ | ✓ | ✓ | 3 | Thick | 2 | 2 |
| 5 | Healthy | 6 | ✓ | ✓ | ✓ | 3 | Thick | 2 | 2 |
| | | 9 | ✓ | ✓ | ✓ | 3 | Thick | 2 | 2 |
| | | 10 | ✓ | X | X | 1 | Thick | 2 | 2 |
| | | 11 | ✓ | ✓ | ✓ | 3 | Thick | 3 | 3 |
| 6 | Healthy | 7 | ✓ | ✓ | X | 2 | Thick | 2 | 2 |
| | | 8 | ✓ | ✓ | ✓ | 3 | Thick | 2 | 2 |
| 7 | Healthy | 7 | ✓ | ✓ | ✓ | 3 | Thick | 1 | 1 |
| | | 8 | ✓ | ✓ | ✓ | 3 | Thick | 1 | 1 |
| | | 9 | ✓ | ✓ | ✓ | 3 | Thick | 1 | 1 |
| | | 10 | ✓ | ✓ | ✓ | 3 | Thick | 1 | 1 |
| 8 | Healthy | 7 | ✓ | ✓ | ✓ | 3 | Thick | 3 | 3 |
| | | 8 | ✓ | ✓ | ✓ | 3 | Thick | 1 | 1 |
| | | 9 | ✓ | X | ✓ | 2 | Thick | 1 | 1 |
| | | 10 | ✓ | X | ✓ | 2 | Thick | 1 | 1 |
| 9 | Healthy | 7 | X | ✓ | X | 1 | Thick | 1 | 1 |
| | | 8 | ✓ | ✓ | ✓ | 3 | Thick | 1 | 1 |
| | | 9 | ✓ | ✓ | ✓ | 3 | Thick | 1 | 1 |
| | | 10 | ✓ | ✓ | ✓ | 3 | Thick | 1 | 1 |
| 10 | Healthy | 7 | ✓ | ✓ | ✓ | 3 | Thick | 2 | 2 |
| | | 8 | ✓ | ✓ | ✓ | 3 | Thick | 2 | 2 |
| | | 9 | ✓ | ✓ | ✓ | 3 | Thick | 2 | 2 |
| | | 10 | ✓ | ✓ | ✓ | 3 | Thick | 2 | 2 |
| 11 | Diseased | 22 | ✓ | ✓ | ✓ | 3 | Thick | 2 | 3 |
| | | 23 | ✓ | X | ✓ | 2 | Thick | 3 | 4 |
| | | 24 | ✓ | ✓ | ✓ | 3 | Thick | 1 | 2 |
| | | 25 | ✓ | ✓ | ✓ | 3 | Thick | 2 | 3 |
| | | 26 | ✓ | ✓ | ✓ | 3 | Thick | 2 | 2 |
| | | 27 | ✓ | ✓ | ✓ | 3 | Thick | 2 | 2 |
| 12 | Diseased | 6 | ✓ | ✓ | ✓ | 3 | Thick | 2 | 3 |
| | | 7 | ✓ | ✓ | ✓ | 3 | Thick | 2 | 3 |
| | | 8 | ✓ | X | ✓ | 2 | Thick | 2 | 2 |
| | | 9 | ✓ | ✓ | ✓ | 3 | Thick | 2 | 3 |
| | | 10 | ✓ | ✓ | ✓ | 3 | Thick | 2 | 3 |
| | | 11 | ✓ | ✓ | ✓ | 3 | Thick | 2 | 3 |
| 13 | Diseased | 6 | ✓ | ✓ | ✓ | 3 | Thick | 1 | 1 |
| | | 7 | ✓ | ✓ | ✓ | 3 | Thin | 1 | 1 |
| | | 8 | ✓ | ✓ | ✓ | 3 | Thin | 4 | 4 |
| | | 9 | ✓ | ✓ | ✓ | 3 | Thin | 7 | 7 |
| | | 10 | ✓ | ✓ | ✓ | 3 | Thin | 2 | 2 |
| | | 11 | ✓ | X | X | 1 | Thin | 6 | 6 |
| 14 | Diseased | 22 | ✓ | ✓ | ✓ | 3 | Thick | 2 | 2 |
| | | 23 | ✓ | ✓ | ✓ | 3 | Thick | 1 | 1 |
| | | 24 | ✓ | ✓ | ✓ | 3 | Thick | 2 | 2 |
| | | 25 | ✓ | ✓ | ✓ | 3 | Thick | 2 | 2 |
| | | 26 | ✓ | ✓ | ✓ | 3 | Thick | 2 | 2 |
| | | 27 | ✓ | ✓ | ✓ | 3 | Thick | 1 | 1 |
| 15 | Diseased | 22 | ✓ | ✓ | ✓ | 3 | Thick | 2 | 2 |
| | | 23 | ✓ | ✓ | ✓ | 3 | Thick | 2 | 2 |
| | | 24 | ✓ | ✓ | X | 2 | Thick | 5 | 5 |
| | | 25 | ✓ | ✓ | ✓ | 3 | Thick | 2 | 2 |
| | | 26 | ✓ | ✓ | ✓ | 3 | Thick | 2 | 2 |
| | | 27 | ✓ | ✓ | ✓ | 3 | Thick | 2 | 2 |
| 16 | Diseased | 22 | ✓ | ✓ | ✓ | 3 | Thick | 2 | 2 |
| | | 23 | ✓ | ✓ | ✓ | 3 | Thick | 2 | 3 |
| | | 24 | ✓ | ✓ | ✓ | 3 | Thick | 2 | 3 |
| | | 25 | ✓ | ✓ | ✓ | 3 | Thick | 1 | 1 |
| | | 26 | ✓ | ✓ | ✓ | 3 | Thick | 2 | 2 |
| | | 27 | ✓ | ✓ | ✓ | 3 | Thick | 2 | 2 |

The invention claimed is:

1. A computer-implemented method for diagnosing or monitoring periodontal disease, comprising:

obtaining one or more B-mode ultrasound images of a dentition and periodontium of a patient;

identifying, on the ultrasound images, at least two anatomical biomarkers selected from a gingival margin (GM), alveolar bone crest (ABC), cementoenamel junction (CEJ), periodontal ligament (PDL), and gingival edge (GE);

determining at least one metric, wherein the metric comprises a quantitative measurement defined as a distance, ratio, or geometric relationship between two or more of the identified biomarkers;

evaluating the metric by comparing it to a predetermined threshold, reference range, or baseline to generate a diagnostic indicator of periodontal health or disease; and based at least in part on the evaluation, performing a therapeutic treatment of the periodontal disease identified by the diagnostic indicator.

2. The method of claim 1 wherein the metric is an IGR metric determined by: determining a distance between the CEJ and GM biomarkers along a plane parallel to a tooth surface defining an image-based gingival recession (iGR) metric associated with recession.

3. The method of claim 1, wherein the metric is a gingival thickness (iGT) measurement, determined by:

determining a first distance between the GM and ABC biomarkers;

determining a facial midpoint along the first distance; and determining a second distance between the facial midpoint and the GE biomarker.

4. The method of claim 3, wherein the therapeutic treatment comprises a gum flap transplant.

5. The method of claim 1, wherein the metric is a gingival height (iGH) measurement, determined by computing a distance between the ABC and GM biomarkers as a surrogate of periodontal pocket depth.

6. The method of claim 5, wherein the therapeutic treatment comprises a gum flap transplant or scalar root planing.

7. The method of claim 1, wherein the metric is an alveolar bone level (iABL) measurement, determined by computing a distance between the ABC and CEJ biomarkers as a surrogate of clinical attachment loss.

8. The method of claim 7 wherein the therapeutic treatment comprises a gum flap transplant or scalar root planing.

* * * * *